(12) United States Patent
Shin et al.

(10) Patent No.: US 11,998,171 B2
(45) Date of Patent: Jun. 4, 2024

(54) PROBE DEVICE DETACHABLY COUPLED TO ENDOSCOPE

(71) Applicants: TAEWOONG MEDICAL CO., LTD., Gimpo-si (KR); Kyong Min Shin, Gyeonggi-do (KR)

(72) Inventors: Kyong Min Shin, Gyeonggi-do (KR); Sung Hwan Park, Seoul (KR); Hyun Soo Ji, Seoul (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 348 days.

(21) Appl. No.: 16/971,205

(22) PCT Filed: Apr. 18, 2019

(86) PCT No.: PCT/KR2019/004705
§ 371 (c)(1),
(2) Date: Aug. 19, 2020

(87) PCT Pub. No.: WO2019/203594
PCT Pub. Date: Oct. 24, 2019

(65) Prior Publication Data
US 2021/0093166 A1    Apr. 1, 2021

(30) Foreign Application Priority Data
Apr. 18, 2018    (KR) .................. 10-2018-0044871

(51) Int. Cl.
*A61B 1/00*    (2006.01)
*A61B 1/005*    (2006.01)
(Continued)

(52) U.S. Cl.
CPC ...... *A61B 1/00105* (2013.01); *A61B 1/00128* (2013.01); *A61B 1/0057* (2013.01); *A61B 1/053* (2013.01); *A61B 1/0684* (2013.01)

(58) Field of Classification Search
CPC ............ A61B 1/00105; A61B 1/00128; A61B 1/0057; A61B 1/053; A61B 1/0684;
(Continued)

(56) References Cited

U.S. PATENT DOCUMENTS 4,203,430 A * 5/1980 Takahashi ............ A61B 1/0052
600/149
5,007,406 A * 4/1991 Takahashi .................. B25J 1/02
600/119
(Continued)

FOREIGN PATENT DOCUMENTS

JP    2000-014628 A    1/2000
JP    2007000427 A *  1/2007 ......... A61B 1/00039
(Continued)

*Primary Examiner* — John P Leubecker
*Assistant Examiner* — Jae Woo
(74) *Attorney, Agent, or Firm* — Bridgeway IP Law Group, PLLC; Jihun Kim (57) ABSTRACT

Provided is an endoscope including a separable probe. The endoscope includes a handle unit and a probe unit detachably mounted on the handle unit. The handle unit includes a first connector reciprocally movable by an adjustment knob. The probe unit includes a probe deformable in response to movement of a wire and a second connector coupled to an end of the wires and detachably coupled to the first connector.

8 Claims, 11 Drawing Sheets

(51) Int. Cl.
*A61B 1/05* (2006.01)
*A61B 1/06* (2006.01)

(58) Field of Classification Search
CPC ..... A61B 1/00091; A61B 1/05; A61B 1/0676; A61B 1/00066; A61B 1/00124; A61B 1/0052; A61B 1/00121
See application file for complete search history.

(56) References Cited

U.S. PATENT DOCUMENTS

| | | | | |
|---|---|---|---|---|
| 2006/0252993 | A1* | 11/2006 | Freed | A61B 1/0052 604/95.04 |
| 2012/0197190 | A1* | 8/2012 | Suon | A61M 25/0113 604/95.04 |
| 2013/0261392 | A1* | 10/2013 | Yamamoto | A61B 1/00006 600/117 |
| 2015/0351610 | A1* | 12/2015 | Fan | A61B 1/0052 600/148 |
| 2016/0150945 | A1* | 6/2016 | Okamoto | A61B 1/00101 600/114 |
| 2017/0078583 | A1* | 3/2017 | Haggerty | H04N 23/55 |
| 2020/0113426 | A1* | 4/2020 | Ito | A61B 1/121 |
| 2021/0145257 | A1* | 5/2021 | Levinson | A61B 1/00066 |

FOREIGN PATENT DOCUMENTS

| | | | |
|---|---|---|---|
| JP | 2007-029167 | A | 2/2007 |
| JP | 2007-000427 | A | 1/2008 |
| JP | 2009-225876 | A | 10/2009 |
| JP | 2013-544617 | A | 12/2013 |
| JP | 2016-512961 | A | 5/2016 |
| KR | 2011-0060785 | A | 6/2011 |
| KR | 20110060785 | A * | 6/2011 |
| KR | 10-1091999 | B1 | 12/2011 |
| KR | 10-2014-0063947 | A | 5/2014 |

* cited by examiner

PROBE DEVICE DETACHABLY COUPLED TO ENDOSCOPE

TECHNICAL FIELD

The present disclosure relates to an endoscope including a separable probe and, more particularly, to an endoscope in which a probe insertable into human bodies may be separated from a handle.

BACKGROUND ART

A medical endoscope is a device directly inserted into a human body subject for examination or treatment in order to examine an internal organ or perform a treatment on the internal organ.

Figure 1:
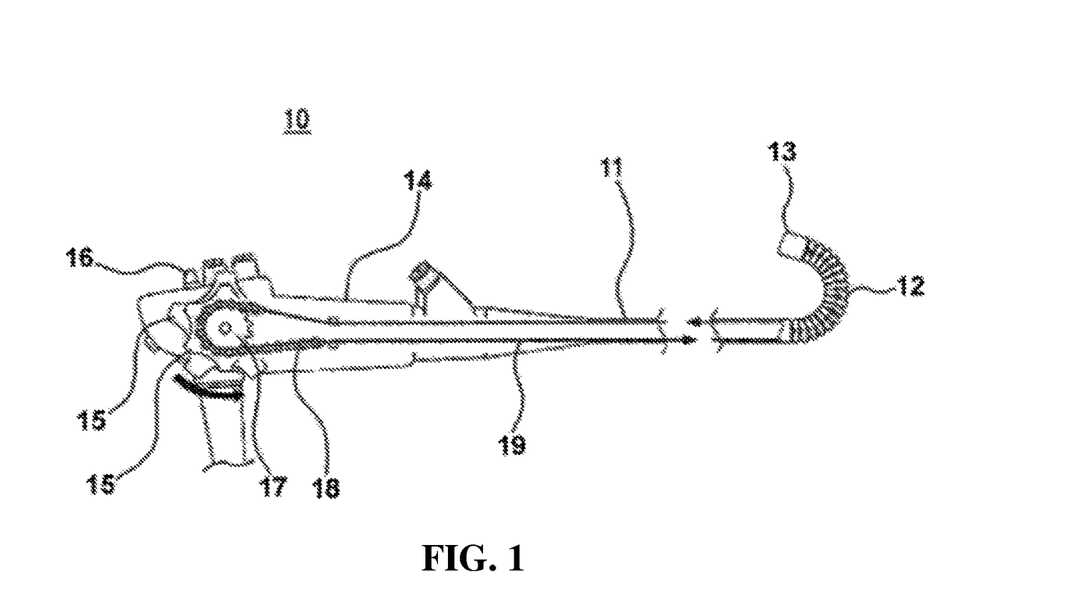
FIG. 1 is a cross-sectional view schematically illustrating a typical endoscope.

FIG. 1 is a cross-sectional view schematically illustrating a typical endoscope 10. Referring to FIG. 1, the endoscope 10 includes an articulation assembly 12 disposed on one end of a flexible insertion tube 11, such that the direction of insertion is adjustable while the endoscope 10 is being inserted into a human body. A leading end body 13 having an image sensor and a light source (or a lens) is mounted on one end of the articulation assembly 12. A handle body 14 is provided on the other end of the insertion tube 11. The handle body 14 is connected to an unshown image processing device through a separable cable and a separable connector.

Dials 15 and buttons 16 used for the direction change and the operation of the articulation assembly 12 are disposed on the handle body 14.

The dials 15 are provided as a pair of dials, by which the direction of movement of the insertion tube 11 may be adjusted to upward, downward, left, and right directions. A sprocket 17 and a chain 18 are provided inside the handle body 14 in order to convert the rotation of the dials 15 into a linear movement. The chain 18 is connected to one end of the articulation assembly 12 via a separate wire 19. As a result, the rotation of the dials 15 is converted into the linear movement of the wire 19 via the sprocket 17 and the chain 18, and the articulation assembly 12 is bent in response to the linear movement of the wire 19. Accordingly, an operator of the endoscope 10 may adjust the direction of movement of the leading end body 13 during the process of inserting the insertion tube 11 into the human body.

Here, since the endoscope is inserted into the human body, thorough hygiene management is required, and the endoscope must be cleaned and sterilized after a diagnosis or a surgery. In some cases, the reuse of a portion of the endoscope actually inserted into the human body, i.e. the insertion tube or the articulation assembly, may be impossible or undesirable. In this case, the entirety of a related-art conventional endoscope device must be replaced, since the entirety of the endoscope device is provided as a single body. In addition, even in a case in which the reuse is possible, cleaning and sterilization work may be more simply performed when the separation of a portion of the endoscope rather than the replacement of the entirety of the endoscope is possible.

Various types of separable endoscopes have been disclosed in the related art. For example, Korean Patent Application Publication No. 10-2014-0063947 discloses an endoscope in which a handle body and an operator body are configured to be detachable. However, in the above patent, since it is not easy to separate and reattach a wire, the other portions rather than the wire are configured to be detachable. Thus, the above patent may have a problem of low efficiency. Even in the case that the attachment and detachment problem of the wire is solved, it is still difficult to accurately operate the endoscope, since the pair of wires spaced apart from each other move different distances due to different radii when the endoscope is bent.

DISCLOSURE

Technical Problem

The present disclosure is derived to meet the aforementioned demands of the related art, and an objective of the present disclosure is to provide an endoscope having a portion easily detachable from and attachable to the endoscope.

Technical Solution

In order to achieve the above objective, according to an aspect of the present disclosure, a probe device detachably coupled to a handle unit of an endoscope is provided. The probe device includes a probe deformable in response to movement of wires and a pair of second connectors coupled to an end of the wires and detachably coupled to the handle unit. The pair of second connectors are disposed to face each other and movable in different directions.

Here, the probe device may further include a first pinion gear disposed between the pair of second connectors. The pair of second connectors include rack gear portions provided on facing surfaces thereof to be engaged with the first pinion gear. One of the pair of second connectors moves in a first direction, the other of the pair of second connectors moves in a second direction opposite to the first direction.

In addition, the probe device may further include another pair of second connectors spaced apart from the pair of second connectors and a second pinion gear engaging with the other pair of second connectors.

The first pinion gear and the second pinion gear are spaced apart from each other in a vertical direction.

The handle unit includes a pair of first connectors able to be coupled to the pair of second connectors. One of the pair of first connectors and one of the pair of second connectors able to be coupled to each other work in concert with each other when moving in a first direction and do not work in concert with each other when moving in a second direction.

One of the pair of first connectors and one of the pair of second connectors able to be coupled to each other engage with each other when moving in the first direction and are separated from each other when moving in the second direction.

The wires are coupled to the pair of second connectors to be relatively movable within limited ranges, respectively.

The wires are connected to the pair of second connectors using wire fixing members, respectively. The wire fixing members are inserted into the pair of second connectors to be slidable and movable within limited ranges, respectively.

The probe device further includes an end cover provided on an end. A printed circuit board is disposed on the end cover.

A light source including one or more light-emitting diodes and an image sensor are mounted on the printed circuit board.

Advantageous Effects

According to an aspect of the present disclosure having the above-described configuration, the wires provided in the handle unit and the probe unit separated from each other may be easily detached and attached using the first and second connectors, so that handle unit and the probe unit may be divided in any portion of the endoscope. In particular, since no separate operations for connecting or disconnecting the wires are required when separating or coupling the handle unit and the probe unit from or to each other, the operations of detaching and attaching the handle unit and the probe unit to and from each other may be significantly easily performed.

In addition, since the endoscope may be divided in any position regardless of the position of the wires, suitable products may be provided according to the respective uses of the endoscope. Accordingly, the components of the endoscope may be reused or replaced more economically, and cleaning and sterilization operations may be performed more easily.

In addition, since the first and second connectors may be allowed to work in concert with each other or prevented from working in concert with each other depending on the travel direction, degradations in operability due to different radii may be overcome.

That is, the wires to which force for bending the probe unit is applied are allowed to work in concert with each other, so that the probe unit is bent in an intended direction and at an intended angle, whereas the wires in the opposite side may remain stopped (since the wires do not work in concert with each other), so that the difference in the travel distance may be absorbed.

BEST MODE

Hereinafter, embodiments of an endoscope having an attachable and detachable probe according to the present disclosure will be described in detail with reference to the accompanying drawings.

Figure 2:
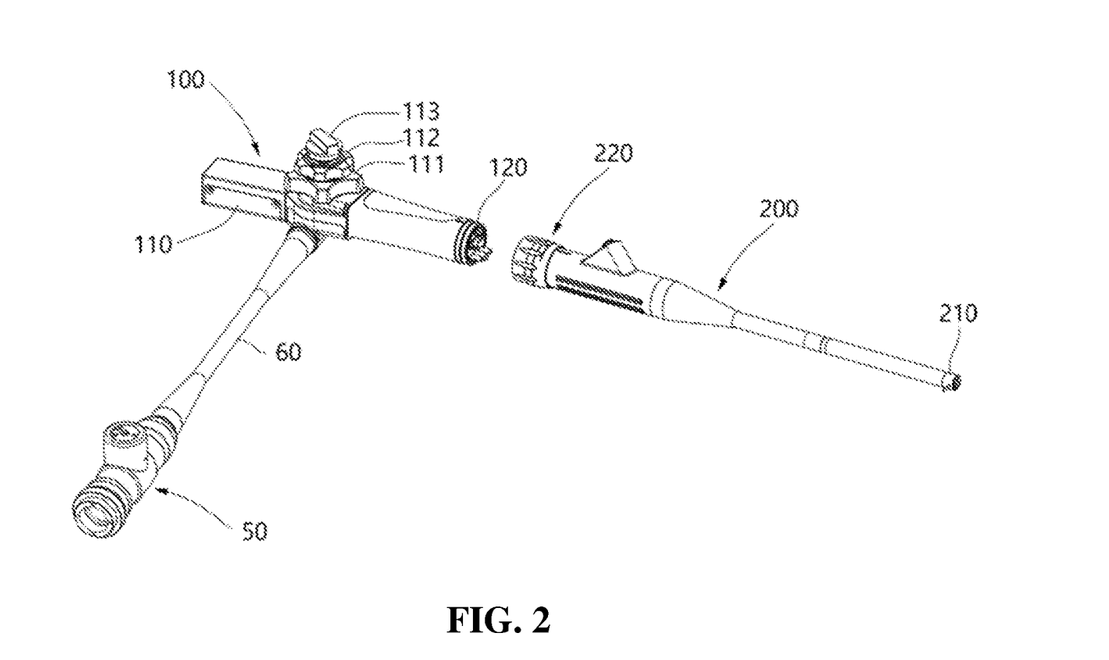
FIG. 2 is an exploded perspective view illustrating an embodiment of an endoscope according to the present disclosure.

Referring to FIG. 2, an embodiment of the endoscope having an attachable and detachable probe according to the present disclosure is illustrated. The present embodiment generally includes a handle unit 100 and a probe unit 200 detachably mounted on the handle unit 100. In addition, the embodiment includes a connector adaptor 50 enabling a connection to an external device. The connector adaptor 50 is connected to the handle unit 100 via a universal cord 60. Here, the connector adaptor 50 and universal cord 60 are illustrative only and are not necessarily limited to the illustrated shapes. Any shapes applicable to the endoscope may be used.

Figure 3:
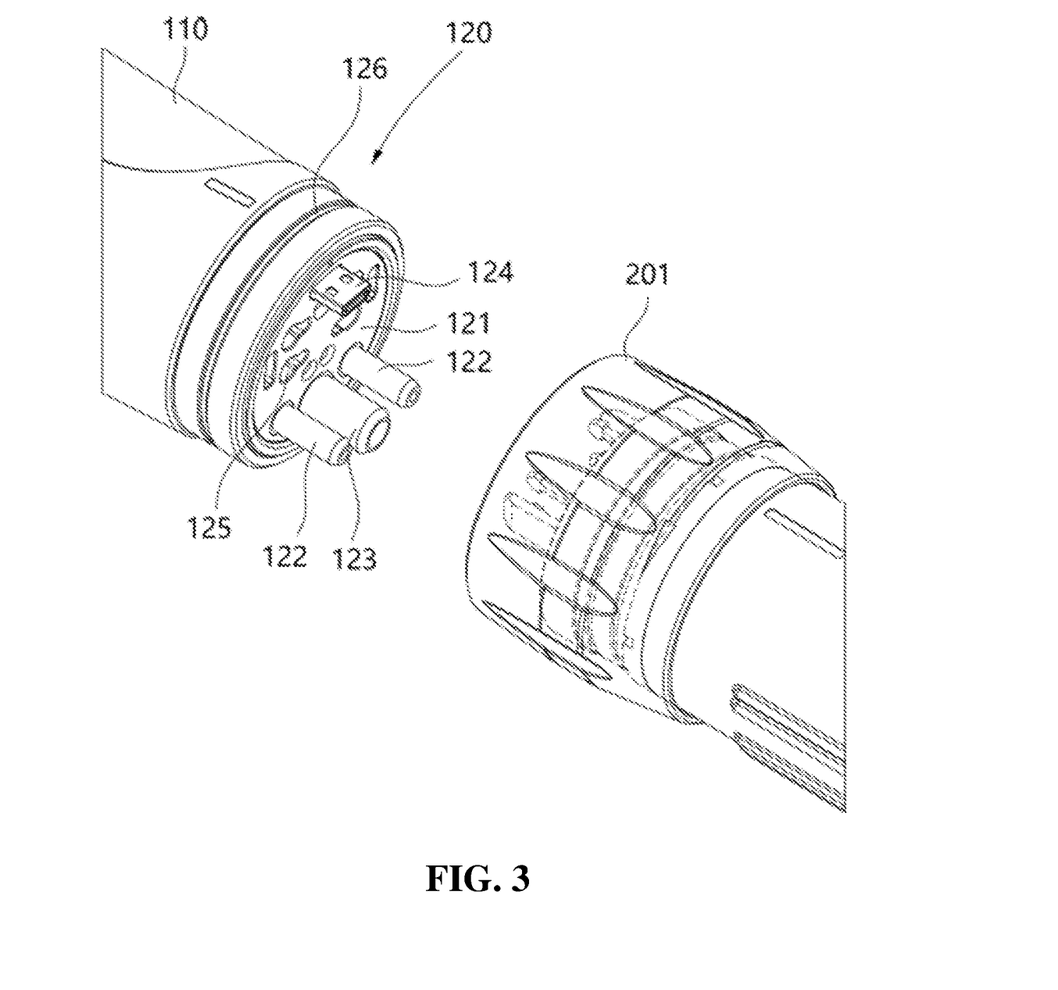
FIG. 3 is an enlarged exploded perspective view illustrating the handle unit and the probe unit in the embodiment illustrated in FIG. 2.

The handle unit 100 includes a body 110 providing a holding volume enabling a practitioner to hold the body 110. The body 110 receives therein a chain and a cable through which the probe unit is driven. Referring to FIG. 3, a handle-side coupler 120 is provided on one end of the body 110. The handle-side coupler 120 has an end cover 121 closing one end of the handle unit 100. The end cover 121 has two supply channels 122, through which air and water are supplied to the affected part during a treatment, and a suction channel 123 provided between the supply channels 122. Each of the air supply channel, the water supply channel, and the suction channel may have a substantially cylindrical shape with a hollow internal space and, when coupled to the probe unit, be inserted into the probe unit such that water, air, or the like may be reliably supplied to a body part under treatment or examination.

A connecting terminal 124 is provided above the channels. The connecting terminal 124 is provided to be electrically connected to the probe unit such that data obtained by a camera or the like provided on one end of the probe unit may be transferred to an external device. For example, the connecting terminal 124 may be a high-definition multimedia interface (HDMI) terminal through which images are transmitted.

A plurality of through-holes 125 are provided between the channel and the connecting terminal. Each of the through-holes serves as a passage allowing a second connector, a stopper releasing member, or the like provided in the probe unit to be inserted into the handle unit therethrough.

The coupler 120 may be configured such that the diameter thereof is smaller than that of the body 110 and have an O-ring provided on the outer circumference thereof, the O-ring preventing the leakage of air, water, or the like.

Returning to FIG. 2, first and second knobs 111 and 112 are provided on the upper portion of one side of the body 110 such that the first and second knobs 111 and 112 are stacked on each other in a vertical direction with respect to FIG. 2. The first and second knobs 111 and 112 are connected to first and second brackets to be described later, respectively, and are configured such that the first and second knobs 111 and 112 may rotate independently of each other. Each of the knobs is provided with a plurality of protruding teeth allowing the practitioner to easily hold and rotate the knob.

Meantime, the first knob may independently rotate with the second knob remaining fixed. In the same manner, the second knob may independently rotate with the first knob remaining fixed. The first knob 111 controls the vertical movement of the probe unit. That is, when the first knob is rotated clockwise or counterclockwise, the end of the probe unit is bent upward or downward. The second knob 112 controls the lateral movement of the probe unit. That is, when the second knob is rotated clockwise or counterclockwise, the end of the probe unit is bent to the left or right.

In this manner, the direction of rotation of the probe unit may be freely adjusted by operating the first and second knobs 111 and 112. In some cases, it may be necessary to fix the probe unit bent at a specific angle. In this regard, a fixing knob 113 is provided above the second knob 112. When the fixing knob 113 is rotated, the first and second sprockets are fixed without rotation. Consequently, the end of the probe unit remains fixed.

The probe unit 200 has a probe 210 provided on one side, the probe 210 being supposed to be inserted into a human body, and a coupler 220 provided on the other side, the coupler 220 being supposed to be coupled to the handle unit 100. The probe 210 may have a camera or the like disposed on the distal end thereof. The probe 210 includes a bendable portion made of a flexible material such that the bendable portion may be bent in the vertical and lateral directions in response to the movement of wires to be described later. A mesh tube 204 (see FIG. 7) protecting the bendable portion may be mounted on an external portion of the bendable portion.

The coupler 220 of the probe unit 200 includes a fixing nut 201 allowing the coupler 220 to be fixed to the handle unit. The fixing nut 201 is configured to surround both a portion of the end of the probe unit and a portion of the end of the handle unit, in particular, the outer circumferential portions of the couplers of the probe unit and the handle unit. In addition, the fixing nut 201 is mounted so as to be rotatable within a predetermined range of angle with respect to the probe unit 200, and may be fastened to or separated from the handle unit depending on the direction of rotation. That is, in a situation in which the two couplers are coupled to each other, when the fixing nut 201 is rotated in one direction, the handle unit is fastened with the fixing nut and remains in a coupled state. When the fixing nut 201 is rotated in the opposite direction, the handle unit 100 and the fixing nut 201 are decoupled from each other, thereby causing the handle unit to be separable from the probe unit.

Figure 4:
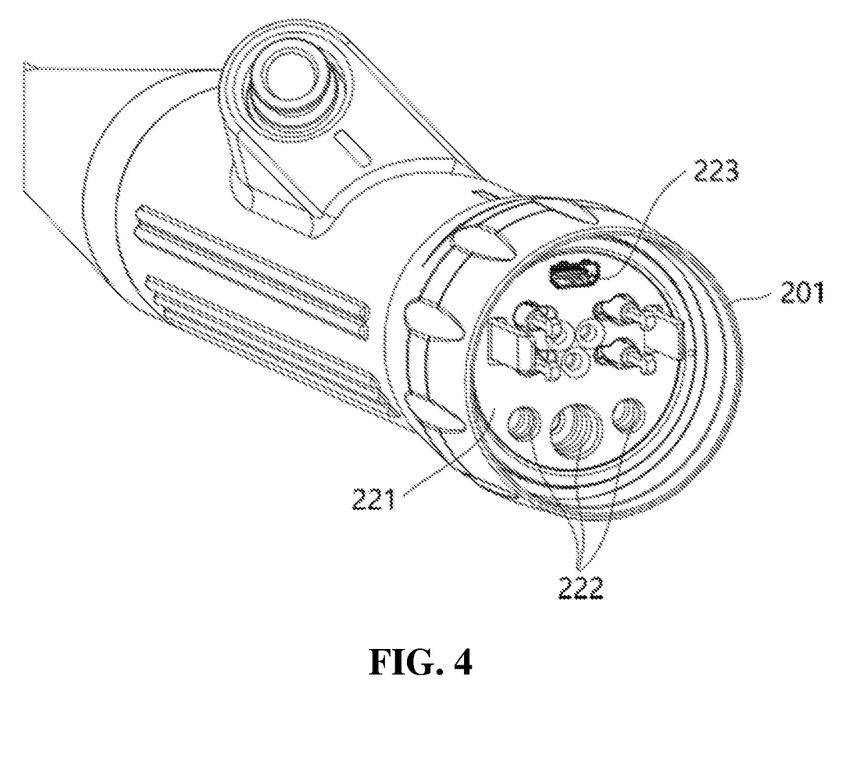
FIG. 4 is an enlarged perspective view illustrating the couplers of the probe unit in the embodiment illustrated in FIG. 2.

FIG. 4 illustrates the coupler 220 of the probe unit 200. Referring to FIG. 4, the coupler 220 includes an end cover 221 closing one end of the probe unit. The end cover 221 has three channel receivers 222 into which the supply channels 122 and the suction channel 123 are inserted. The respective channel receivers 222 have the shape of a hollow cylinder, and are configured such that the inner diameters thereof correspond to the outer diameters of the channels to be inserted thereinto. In addition, an O-ring preventing the leakage of air, water, or the like to be supplied may be provided inside each of the channel receivers.

Another connecting terminal 223 corresponding to the foregoing connecting terminal is provided on the opposite side of the channel receivers 222. That is, while the handle unit has a male terminal and the probe unit has a female terminal, the opposite configuration is also possible.

The ends of the four second connectors and the stopper releasing members are disposed and protrude between the channel receivers 222 and the connecting terminal 223. This feature will be described later.

Hereinafter, the internal structure of the handle unit 100 will be described with reference to FIG. 5.

Figure 5:
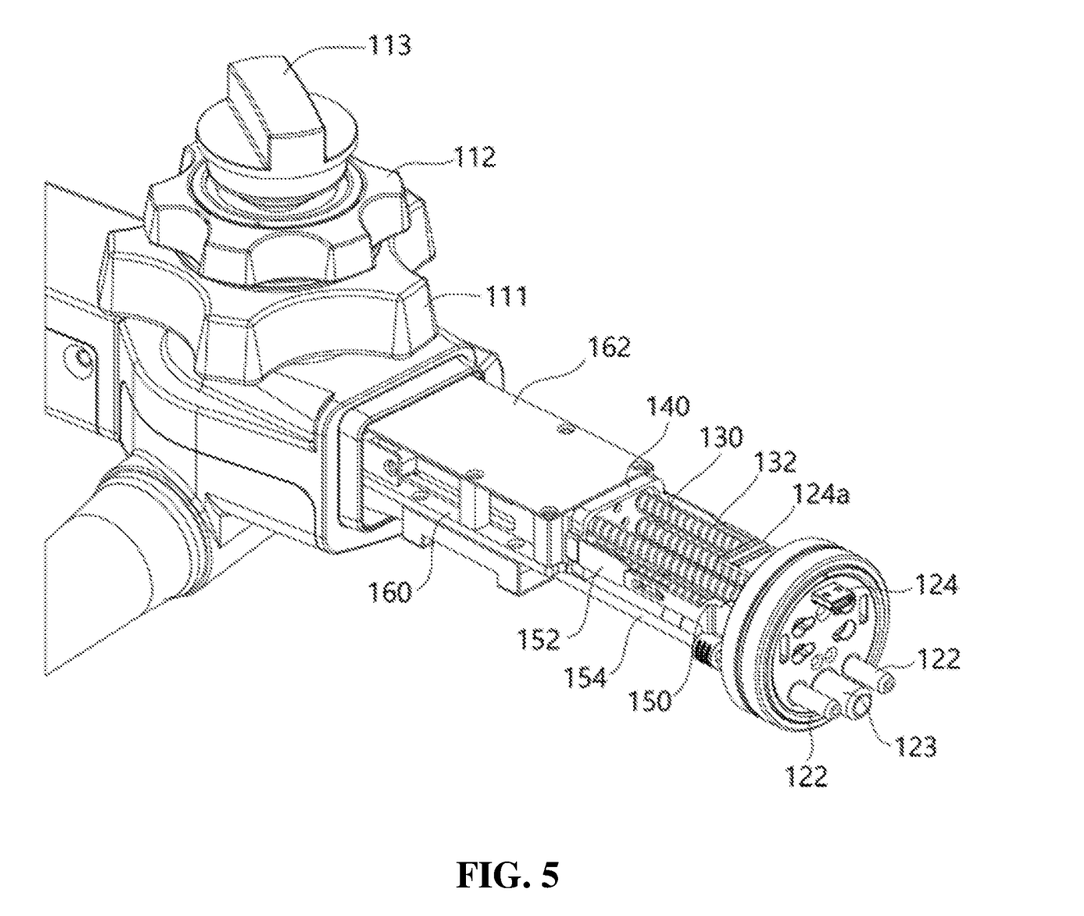
FIG. 5 is a perspective view illustrating the internal structure of the handle unit in the embodiment illustrated in FIG. 2.

Referring to FIG. 5, a printed circuit board (PCB) 124*a* is disposed adjacent to the connecting terminal 120 of the handle unit 100. The PCB 124*a* is electrically connected to the connecting terminal 120 and controls the operation of the connecting terminal.

In addition, four first connectors 130 are disposed adjacent to the end cover 121. The four first connectors 130 are respectively shaped as a hollow pipe with the interior thereof being hollow, and are arranged to form a rectangle when viewed from the front. A connector guide plate 140 is disposed on the knob-side end of the first connectors 130. The connector guide plate 140 includes guide holes (not shown) into which the four first connectors 130 are inserted. Each of the first connectors 130 is slidably mounted within the guide hole. That is, the connector guide plate 140 serves to not only fix the first connectors but also to guide the sliding movement of the first connectors. An arm 152 extending in the longitudinal direction of the first connector is fixedly disposed on the connector guide plate 140.

In addition, return springs 132 are mounted on the outer circumferential portions of the first connectors 130. When no external force is applied, elastic force of returning the first connectors 130 to the position illustrated in FIG. 5 is applied. During the operation, the first connectors 130 are caused to slide from the position illustrated in FIG. 5 toward the knobs, using the first and second knobs. However, when force applied to the knobs is removed, the return springs restore the first connectors to the position illustrated in FIG. 5.

The two first connectors disposed in the lower positions with respect to FIG. 5 are in concert with the operation of the first knob 111. That is, when the first knob 111 is rotated, the lower first connectors rotate the probe up and down while moving. In addition, the two first connectors disposed in the upper positions are in concert with the operation of the second knob 112. When the second knob 112 is rotated, the first connectors rotate the probe to the left and right while moving.

A single stopper 150 is disposed to the left of the first connectors 130, and another single stopper 150 is disposed to the right of the first connectors 130. As illustrated in FIG. 5, the stoppers 150 are located adjacent to the first connectors 130. In the present embodiment, the stoppers 150 are placed on specific surface portions of the arm 152 while being separated from the arm 152. However, the stoppers 150 are not limited thereto, but may be disposed to be completely separated from the arm 152. The operation of the stoppers will be described later. Supply pipes 154 connected to the supply channels 122 and the suction channel 123 are disposed below the first connectors 130. The supply pipes may be connected to external sources to supply water, air, and the like to the supply channels 122 or may take in water, air, and the like through the suction channel 124.

A base plate 160 is disposed to the lower left of the connector guide plate 140. The base plate 160 serve as a support portion supporting a variety of components provided within the handle unit 100, and have the shape of a thin plate. The sprockets and chains to be described later are disposed in the upper portion of the base plate 160, and the protective plate 162 is disposed above the sprockets, chains, and the like. The base plate 160 and the protective plate 162 work in concert to define an internal space. The defined internal space is used as a space through which the chain and end wires to be described later move.

Figure 6:
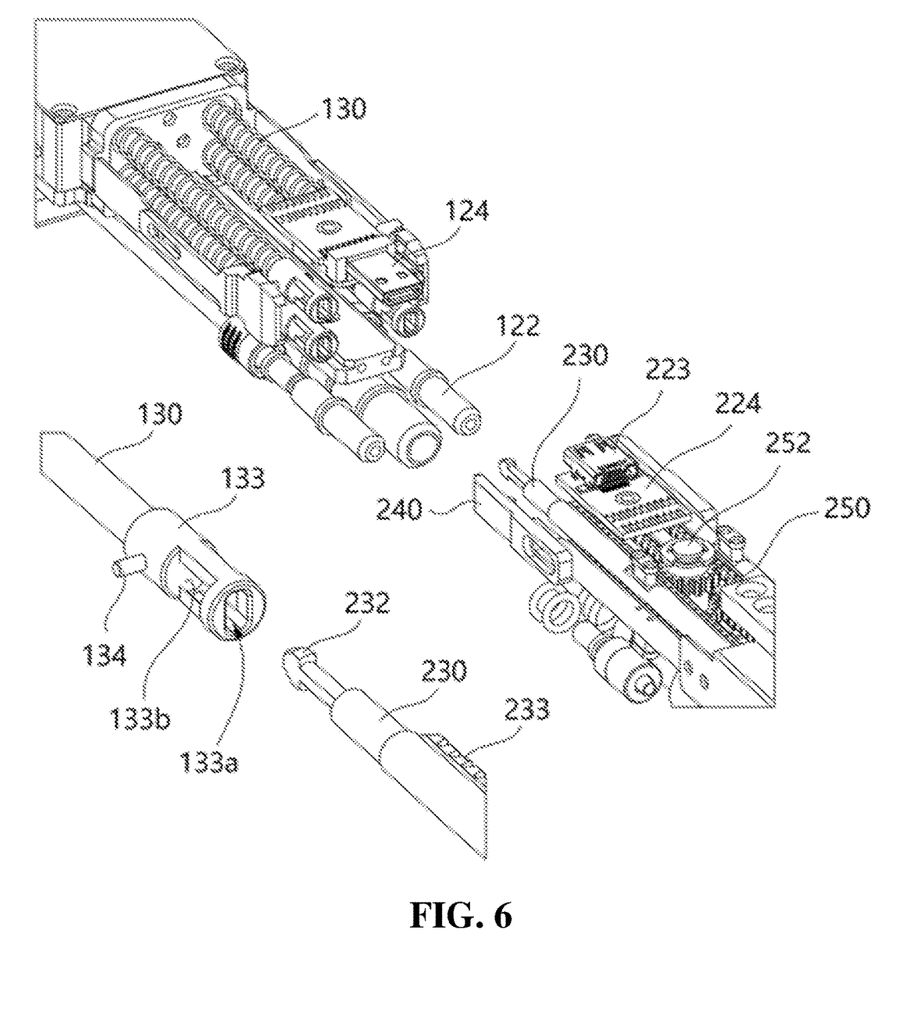
FIG. 6 is an enlarged exploded perspective view illustrating the internal structures of the couplers of the handle unit and the probe unit in the embodiment illustrated in FIG. 2.

Referring to FIG. 6, both the internal structure of the handle unit 100 and the internal structure of the probe unit 200 are illustrated. Referring to FIG. 6, each of the first connectors 130 has an end tip 133 provided on one end thereof adjacent to the probe unit. The diameter of the end tip 133 is increased compared to those of the other portions of each of the first connectors 130, and the end of the end tip 133 is open to form an insertion hole 133a. The insertion hole 133a has the shape of a slit elongated in one direction. In addition, the end tip 133 has cut portions 133b formed in the left and right portions thereof, adjacent to the open end. Thus, stepped portions are provided between the cut portions 133b and the open end.

In addition, a guide pin 134 is provided on a side surface of the end tip 133. The guide pin 134 is fitted into a guide recess to be described later. During sliding movement of the first connectors 130, the guide pin 134 causes the first connector to slide while rotating about the longitudinal axis thereof.

Meanwhile, the connecting terminal 223 disposed in the coupler 220 of the probe unit 200 is electrically connected to the PCB 224 in the same manner as in the handle unit. In addition, four second connectors 230 are disposed below the PCB 224.

When the probe unit is coupled to the handle unit, the four second connectors 230 are inserted into the above-described first connectors, respectively. Specifically, a substantially conical insertion protrusion 232 is provided on one end of each of the second connectors 230 adjacent to the handle unit. The insertion protrusion 232 has a size and shape that may be inserted into the insertion hole 133a provided in each of the end tips 133 of the first connectors described above. The width of the end of the insertion protrusion 232 is increased compared to those of the other portions of the insertion protrusion 232. This configuration allows the insertion protrusion 232 to be engaged with the stepped portion provided in the end tip of the first connector described above, so that the first connectors and the second connectors work in concert with each other. This feature will be described later.

In addition, a single stopper releasing member 240 is disposed to the left of the second connectors, and another single stopper releasing member 240 is disposed to the right of the second connectors. Each of the stopper releasing members 240 is configured such that one end thereof has a tapered surface and extends in the longitudinal direction. In addition, each of the stopper releasing members 240 has a length that may be inserted into the stopper 150 through the end cover disposed on the end of the handle unit when the probe unit is mounted on the handle unit. When the stopper releasing member is inserted into the stopper, the stopper moves away from the first connectors. As a result, the stopper and the first connectors are decoupled from each other. This feature will be described later.

Figure 7:
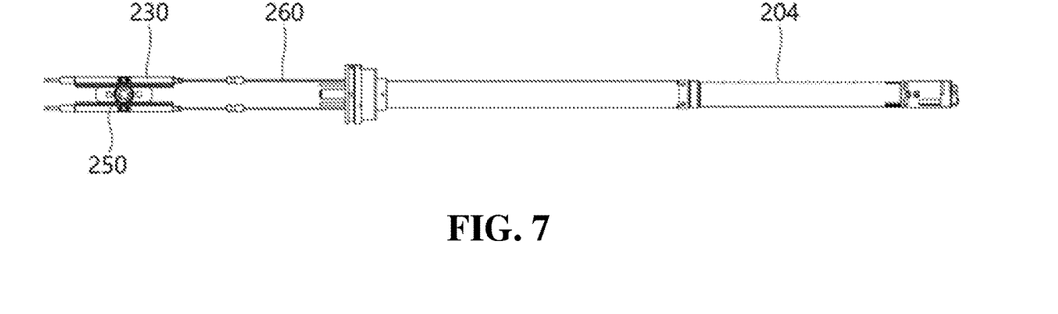
FIG. 7 is a plan view illustrating a portion of the interior of the probe unit in the embodiment illustrated in FIG. 2.
Figure 8:
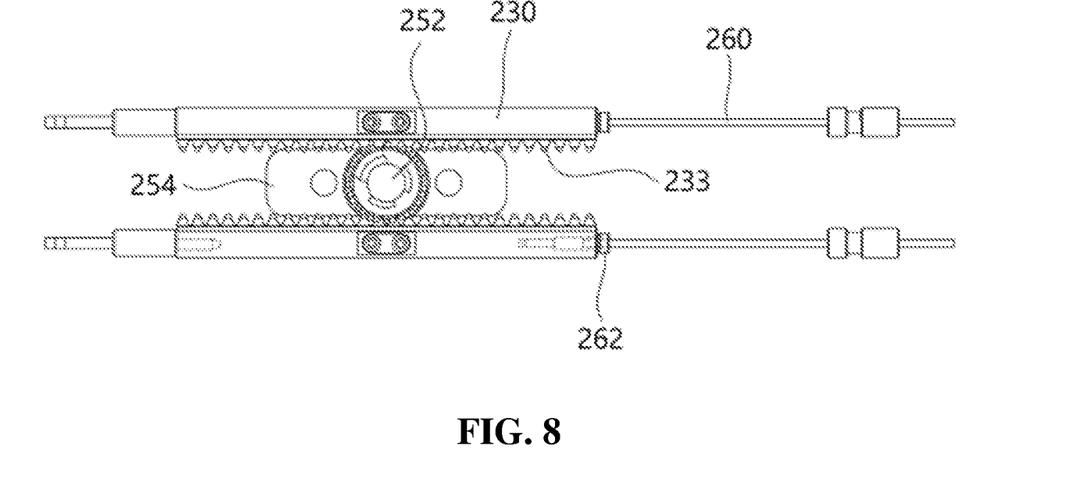
FIG. 8 is an enlarged plan view illustrating portions of FIG. 7.
Figure 9:
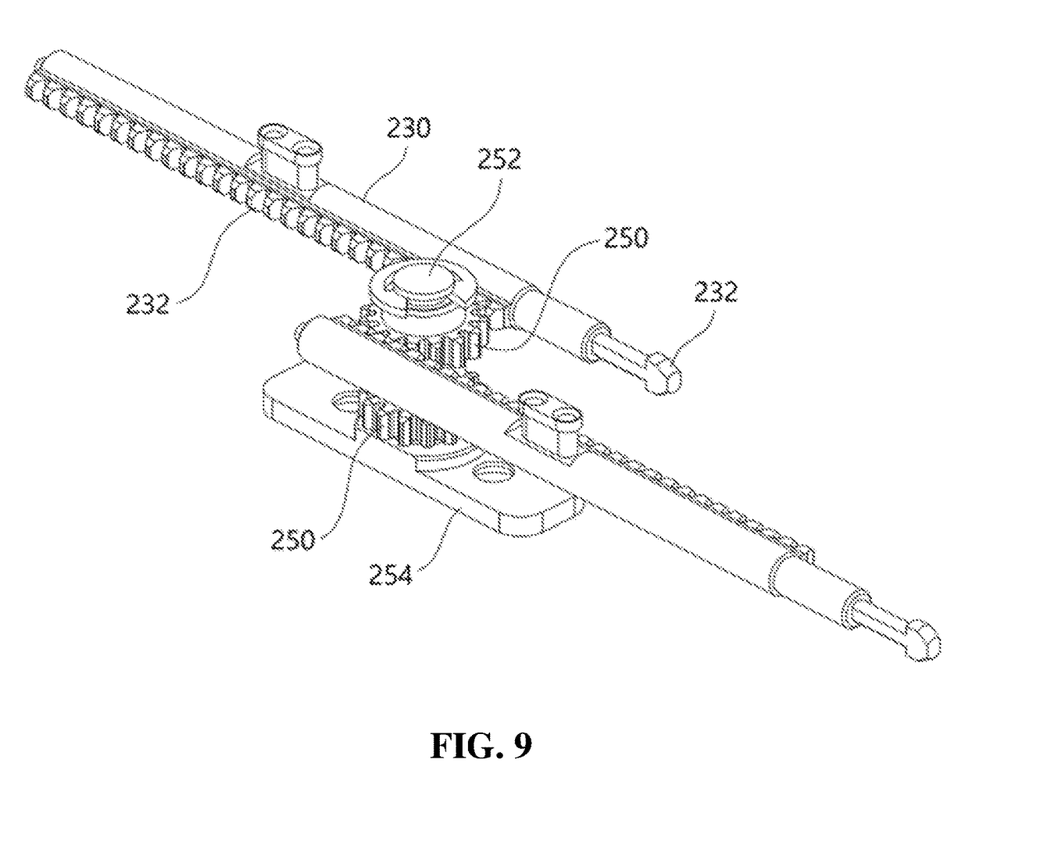
FIG. 9 is a perspective view illustrating the second connector and the pinion gear in FIG. 7.

Meantime, rack gear portions 233 are provided on side surfaces of the second connectors 230. Referring to FIGS. 7 to 9, the rack gear portions 233 are provided on facing surfaces of each pair of second connectors facing each other. That is, the rack gear portions 233 are provided on the facing surfaces of one pair of second connectors disposed in the lower position and in charge of vertical movement of the probe and on the facing surfaces of the other pair of second connectors disposed in the upper position and in charge of lateral movement of the probe, respectively.

Pinion gears 250 engaged with the rack gears are further provided. Two pinion gears 250 are spaced apart from each other in the vertical direction. The pinion gear 250 provided in the lower position is engaged with the rack gear portions provided on the pair of second connectors in charge of the vertical movement of the probe, while the pinion gear 250 provided in the upper position is engaged with the rack gear portions provided on the pair of second connectors in charge of the lateral movement of the probe.

Each of the pinion gears 250 is provided to rotate about a rotary shaft disposed perpendicularly to the longitudinal direction of the second connector. The rotary shaft 252 is rotatably mounted on a rotary shaft support plate 254 disposed below the second connector.

In addition, wires 260 by which the probe is moved are mounted on the other ends of the second connectors 230. Here, each of the wires 260 is not fastened to the corresponding second connector, and may be mounted to be received in the second connector by a predetermined distance. That is, as illustrated in FIG. 8, the wires 260 are connected to the second connectors through wire fixing members 262, respectively. The wire fixing members 262 may be inserted into the second connectors until the stepped portions provided on the ends are in contact with the second connectors.

In other words, the wire fixing members 262 are movable by sliding with respect to the second connectors within a predetermined distance. However, when the predetermined distance is exceeded, the wire fixing members 262 move together with the second connectors. Such a slide travel distance may compensate for the difference in the movement between the wire located inside with respect to the radial direction and the wire located outside with respect to the radial direction.

A pair of second connectors facing each other may be moved in the opposite directions by the pinion gears 250. Here, for the sake of brevity, the direction in which the second connectors move toward the handle unit will be referred to as a shrink direction, while the direction in which the second connectors move away from the handle unit will be referred to as a relaxation direction. In a situation in which the probe unit is coupled to the handle unit, when no external force is applied, i.e. the first or second knob is not operated, the second connectors are aligned in positions illustrated in FIG. 7. When the first or second knob is rotated, one of the first connectors connected to the rotated knob moves in the shrink direction. Here, the other first connector remains in the position (hereinafter, referred to as the "neutral position") in which no external force is applied, instead of moving in the relaxation direction.

Here, the second connector working in concert with the first connector moving in the shrink direction is moved in the shrink direction by the first connector. This movement of the second connector causes the other second connector engaged therewith to move in the relaxation direction. That is, in the shrink direction, the first and second connectors work in concert and move together in the movement. In contrast, in the movement in the relaxation direction, the first connector remains in the neutral position, and only the second connector moves in the relaxation direction. Thus, the first and second connectors are separated from each other in the relaxation direction.

Accordingly, external force is applied to the probe subject in both the shrink direction and the relaxation direction, rather than in a single direction, thereby enabling more accurate and immediate sense of operation to be obtained. In addition, since the travel distance of the wire positioned in the shrink direction is shorter than the travel distance of the wire positioned in the relaxation direction, such a difference in the travel distance needs to be absorbed. In the above-described embodiment, in the relaxation direction, the first and second connectors are separated from each other, such that the second connector may freely move without being held by the first connector, thereby efficiently absorbing the difference in the travel distances as described above. In addition, as described above, the slide coupling between the second connectors 230 and the wires 260 serves as a buffer absorbing the difference in the travel distances described above.

Figure 10:
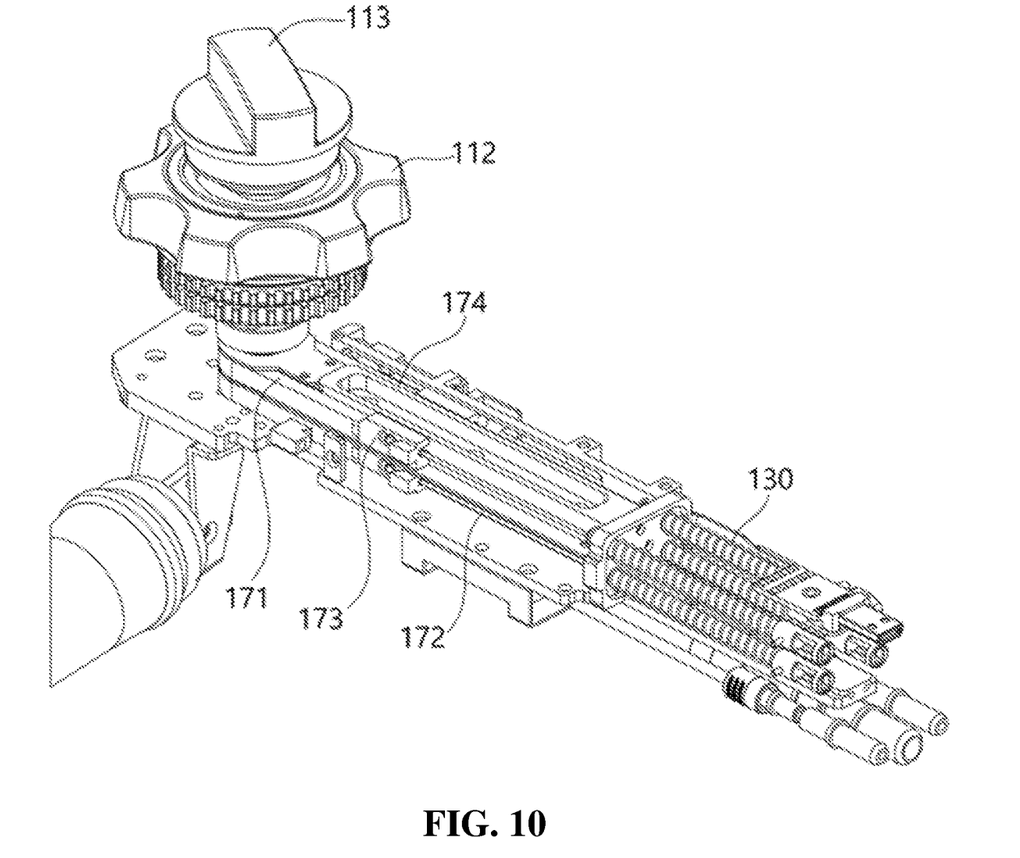
FIG. 10 is a perspective view illustrating the interior of the handle unit in the embodiment illustrated in FIG. 2.
Figure 11:
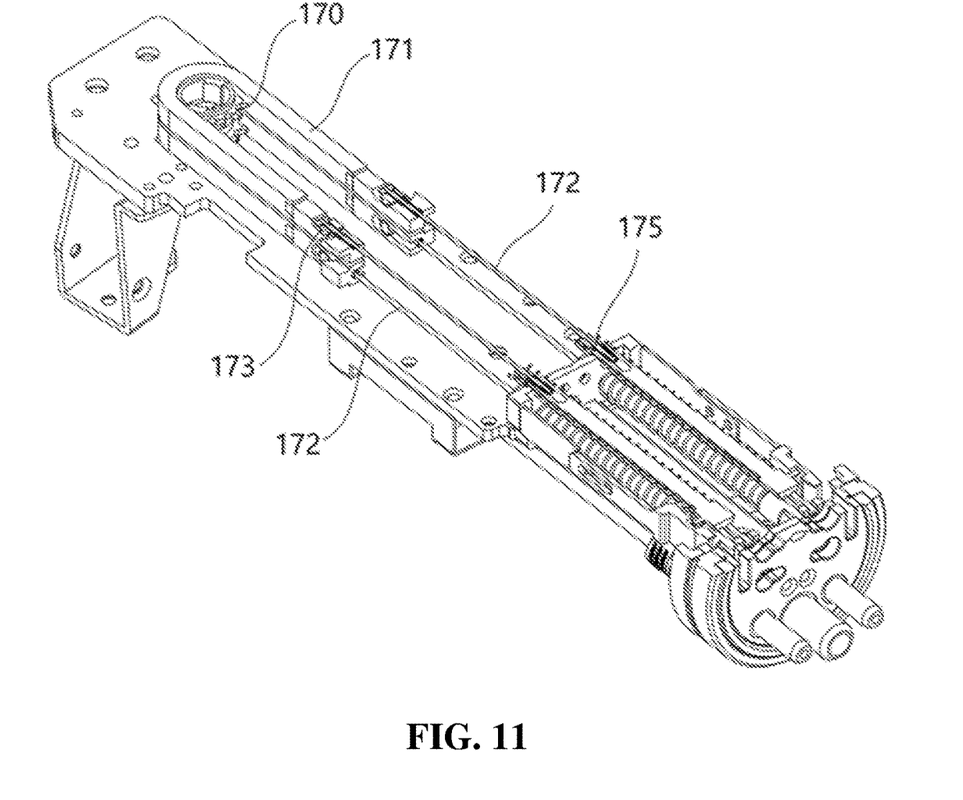
FIG. 11 is a partial cutaway view illustrating the interior of the handle unit in the embodiment illustrated in FIG. 2.
Figure 12:
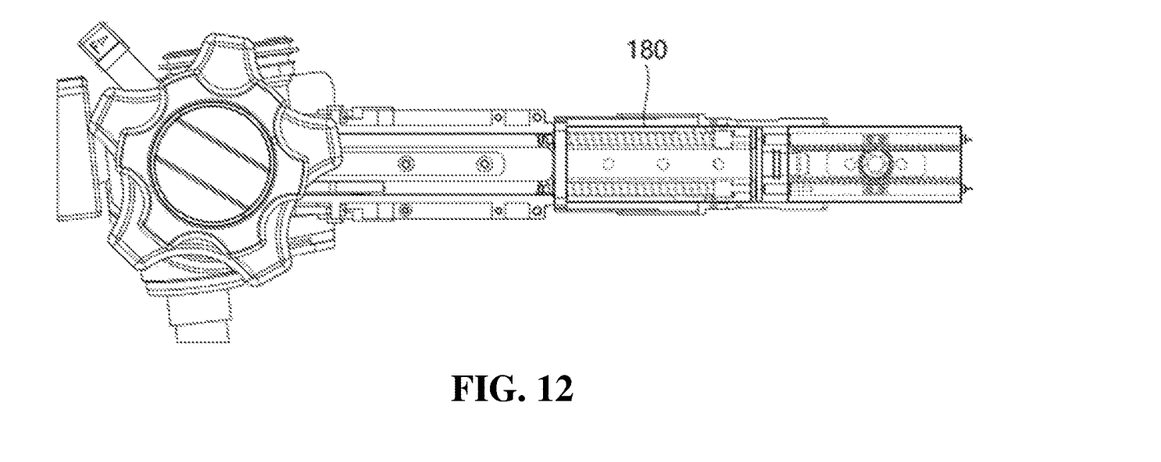
FIG. 12 is a plan view illustrating the state in which the handle unit and the probe unit are coupled in the embodiment illustrated in FIG. 2.

FIGS. 10 and 11 are perspective views illustrating the internal structure of the handle unit. Referring to FIGS. 10 and 11, two sprockets 170 are mounted below the first and second knobs 111 and 112 such that the sprockets 170 may rotate in concert with the rotation of the first and second knobs.

In addition, a chain 171 moving in engagement with each of the sprockets is provided. Both ends of the chain 171 are coupled to end wires 172, and wire couplers 173 are provided between the ends of the chain 171 and the end wires 172. Chain guides 174 disposed adjacent to the wire couplers 173 guide the movement of the wire couplers 173 by contact.

The chain guide 174 has the shape of a hollow rectangular cuboid. A side surface of the chain guide 174 serves as a guide surface by contact with the wire coupler 173. Thus, the chain may reliably move due to the chain guide 174, regardless of whether the chain moves in the shrink direction or the relaxation direction.

The end wires 172 are coupled to the first connectors 130. Specifically, as illustrated in FIG. 11, the end wires 172 are coupled to the first connectors 130 and wire fixing members 175 in the same manner as in the second connectors. The wire fixing members 175 are disposed within the insertion holes formed in the ends of the first connectors 130 such that the wire fixing members 175 may slide within a limited range. Here, regarding the sliding movement, both the wire fixing members and the first connectors may be configured to directly move without sliding in the case of the movement in the shrink direction and to slide only in the case of the movement in the relaxation direction.

The pair of chains are in charge of the vertical movement and the lateral movement of the probes, respectively, and may move independently of each other. In addition, when the chain is moved in response to the rotation of the sprockets, the first connectors positioned in the shrink direction move in the shrink direction, whereas the first connectors positioned in the relaxation direction remain in the neutral position instead of moving in the relaxation direction, due to the coupling structure of the wire fixing members described above.

The first connectors are accommodated in a connector housing 180. The connector housing 180 has the shape of a rectangular cuboid, and has the internal space in which the first connectors 130 may be slidably received. In addition, the connector housing 180 has guide recesses 182 engaging with guide pins 134 provided on the end tip 133.

Each of the guide recesses 182 starts from a side surface of the connector housing 180 and extends in the longitudinal direction to be inclined toward the upper end of the connector housing 180. That is, the start point of the guide recess 182 is in the side surface of the connector housing, while the end point of the guide recess 182 is in the top surface of the connector housing. Thus, the first connectors rotate about 90° about the axes thereof due to the guide pins 134 and the guide recesses 182 while moving in the shrink direction.

In the neutral position, the insertion protrusions 232 of the second connectors 230 remain inserted in the insertion holes 133a of the end tip 133, but the first connectors do not work in concert with the second connectors. This is because the insertion protrusion 232 may be easily released from the insertion holes 133a when the first connectors move. Accordingly, no separate operations for connecting the wires provided in the handle unit and the probe unit are required when coupling or decoupling the handle unit and the probe unit to or from each other.

When the first or second knob is rotated after the coupling, one of the first connectors working in concert with the knobs moves in the shrink direction. In this case, the first connectors 130 move while rotating about 90° about the axes thereof, due to the guide pins 134 and the guide recesses 182, so that the rear surfaces of the insertion protrusions 232 protrude from the cut portions 133b of the end tips 133 and are caught by the stepped portions. Consequently, when the first connectors move in the shrink direction, the second connectors move responsively, so that the probe is deformed in a predetermined direction.

When external force is removed, the first connectors are restored to the neutral positions by the return springs and are then rotated 90° about the axes thereof in the reverse direction due to the guide pins and the guide recesses, so that the insertion protrusions may be released from the insertion holes. As a result, no separate operations for connecting or disconnecting the wires are required when fastening or separating the handle unit and the probe unit, so that the handle unit and the probe unit may be significantly easily attached to and detached from each other.

When the first and second knobs are operated in a position in which the handle unit is separated, the first connectors may be damaged during movement. Thus, it may be necessary to prevent such an operation.

Figure 13:
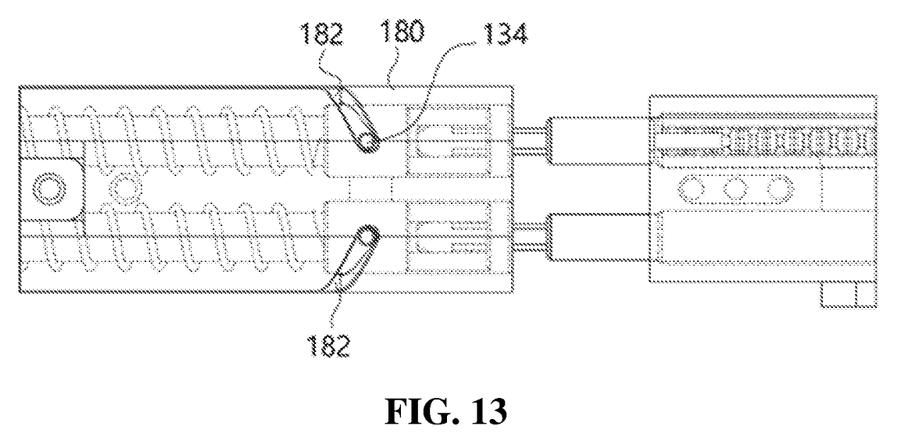
FIG. 13 is a side view illustrating the state in which the handle unit and the probe unit are coupled to each other in the embodiment illustrated in FIG. 2.
Figure 14:
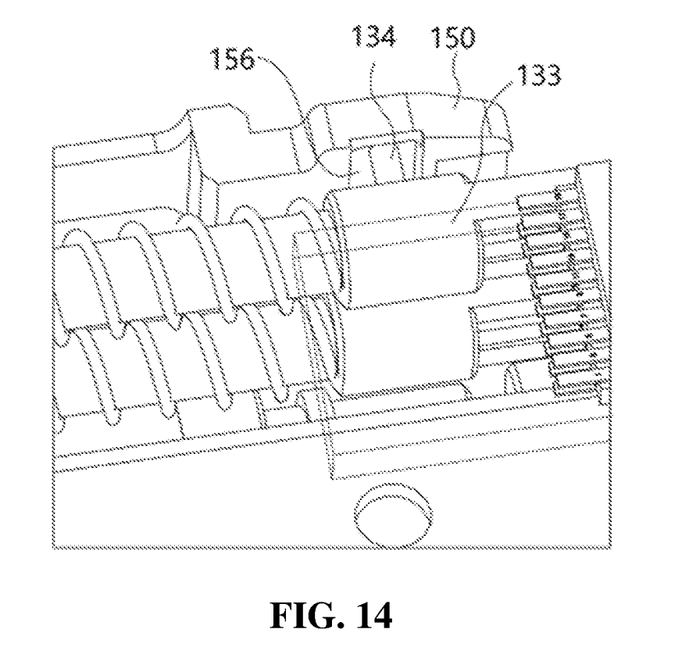
FIG. 14 is an enlarged perspective view illustrating the stopper in the embodiment illustrated in FIG. 2.

Referring to FIG. 14, each of the above-described stoppers 150 has a guide pin recess 156 in the inner surface thereof. The guide pin recess 156 has a depth and width allowing two guide pins 134 disposed adjacent to each other, as illustrated in FIG. 13, to be accommodated therein. The length of the guide pin recess 156 is determined such that both the two guide pins in the neutral position may be accommodated in the guide pin recess 156. In some cases, a plurality of guide pin recesses accommodating the guide pins, respectively, may be formed.

When the guide pins are accommodated in the guide pin recesses, the movement of the guide pins is stopped by the inner walls of the accommodation recesses. Thus, even when it is intended to rotate the first or the second knob, the guide pins are stopped and the movement thereof is prevented by the accommodation recesses, thereby making the rotation of the knob impossible. This is the case in which the handle unit is separated from the probe unit. In contrast, when the handle unit is coupled to the probe unit, the stopper releasing members 240 are inserted between the stoppers 150 and the guide pins 134 and the guide pins are separated from the guide pin recesses 156. In addition, in a position in which the probe unit is coupled to the handle unit, the stopper releasing members 240 are disposed inside the stoppers, thereby preventing the guide pins from being recoupled to the guide pin recesses.

Accordingly, the knobs may be allowed to operate only when the handle unit is coupled to the probe unit, thereby preventing the device from being damaged by an accidental operation in a position in which the handle unit and the probe unit are separated from each other.

Figure 15:
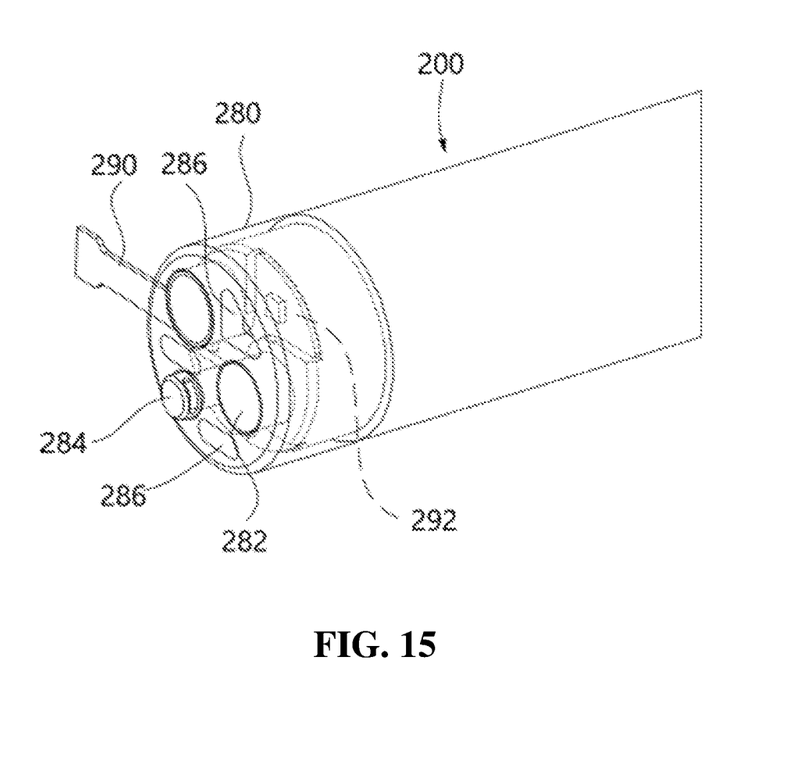
FIG. 15 is an enlarged perspective view illustrating one end of the probe unit in the embodiment illustrated in FIG. 2.

Referring to FIG. 15, an end cover 280 is provided on one end of the probe unit 200. The end cover 280 has a flat cylindrical structure, and is coupled to the end of the probe unit 200. In addition, an image sensor 282 capturing images from the part under examination and a nozzle pipe injecting air and water are mounted on the end cover 280. In addition, the end cover 280 has a plurality of transparent windows 286 provided in a plurality of portions. The transparent windows 286 are implemented as a sheet made of glass or a transparent material, and have a structure able to emit light generated by a light source.

A flexible printed circuit board (PCB) 290 is disposed on the rear surface of the end cover 280, and a plurality of light-emitting diodes (LEDs) 292 are mounted on the flexible PCB 290. The plurality of LEDs 292 may be disposed in portions facing the above-described transparent windows 286 to emit light to the part under examination. The above-described image sensor 282 is also mounted on the flexible PCB. Since the plurality of LEDs are used as the light source, the intensity of light may be easily adjusted and the quantity of emitted light may be significantly increased compared to those of existing halogen lamps, thereby further improving the clarity of images obtained using the image sensors.

The invention claimed is:

1. A probe device detachably coupled to a handle unit of an endoscope, the probe device comprising:
    a probe deformable in response to movement of wires; and
    a pair of second connectors coupled to an end of the wires and detachably coupled to the handle unit, the pair of second connectors being disposed to face each other and movable in different directions,
    wherein the handle unit comprises:
    a first knob and a second knob configured to be rotated independently from each other; and
    a pair of first connectors configured to be coupled to the pair of second connectors,
    wherein one of the pair of first connectors is in concert with an operation of the first knob and the other of the pair of first connectors is in concert with an operation of the second knob,
    wherein one of the pair of first connectors and one of the pair of second connectors are configured to be engaged with each other when moving in a first direction and separated from each other when moving in a second direction,
    wherein each of the pair of first connectors comprises an end tip having an insertion hole formed to extend from a distal end surface of the end tip in an axial direction of the end tip, and a cut portion formed on a side surface of the end tip, an opening of the insertion hole being defined on the distal end surface to be closed along an entire circumference of the opening and to have a shape of a slit elongated in a radial direction perpendicular to the axial direction, and
    wherein each of the pair of second connectors comprises an insertion protrusion extending in the axial direction and configured to be inserted into the insertion hole, and the insertion protrusion has a head including a portion having a greater width in the radial direction than other portions of the head, such that when the insertion protrusion is inserted into the insertion hole and rotated inside the insertion hole, the head of the insertion protrusion protrudes through the cut portion and the insertion protrusion is fastened to the end tip in response to the rotation of the insertion protrusion.

2. The probe device of claim 1, further comprising a first pinion gear disposed between the pair of second connectors,
    wherein the pair of second connectors comprise rack gear portions provided on facing surfaces thereof to be engaged with the first pinion gear, and
    when one of the pair of second connectors moves in a first direction, the other of the pair of second connectors moves in a second direction opposite to the first direction of the one of the pair of second connectors.

3. The probe device of claim 2, further comprising:
    another pair of second connectors spaced apart from the pair of second connectors; and
    a second pinion gear engaging with the other pair of second connectors.

4. The probe device of claim 3, wherein the first pinion gear and the second pinion gear are spaced apart from each other in a vertical direction.

5. The probe device of claim 1, wherein the wires are coupled to the pair of second connectors to be relatively movable within limited ranges, respectively.

6. The probe device of claim 5, wherein the wires are connected to the pair of second connectors using wire fixing members, respectively, the wire fixing members being inserted into the pair of second connectors to be slidable and movable within limited ranges, respectively.

7. The probe device of claim 1, further comprising an end cover provided on an end,
    wherein a printed circuit board is disposed on the end cover.

8. The probe device of claim 7, wherein a light source including one or more light-emitting diodes and an image sensor are mounted on the printed circuit board.

* * * * *